United States Patent [19]

Grohe et al.

[11] Patent Number: 4,556,658

[45] Date of Patent: Dec. 3, 1985

[54] 7-AMINO-1-CYCLOPROPYL-6,8-DIFLUORO-1,4-DIHYDRO-4-OXO-QUINOLINE-3-CARBOXYLIC ACIDS AND ANTIBACTERIAL AGENTS CONTAINING THESE COMPOUNDS

[75] Inventors: Klaus Grohe, Odenthal; Uwe Petersen, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 603,480

[22] Filed: Apr. 24, 1984

[30] Foreign Application Priority Data

May 18, 1983 [DE] Fed. Rep. of Germany ....... 3318145

[51] Int. Cl.$^4$ .................. A61K 31/495; C07D 401/04
[52] U.S. Cl. ..................................... 514/254; 514/222; 514/236; 514/312; 514/256; 544/63; 544/128; 544/358; 544/363; 544/58.6; 544/96; 546/156
[58] Field of Search ............... 544/363, 128, 63, 58.6; 546/156; 424/250, 246, 248.56, 258; 514/222, 236, 254, 312

[56] References Cited

U.S. PATENT DOCUMENTS 3,149,104  9/1964  Lesher et al. ....................... 546/156

FOREIGN PATENT DOCUMENTS

| 2939786 | 4/1980 | Fed. Rep. of Germany | 544/363 |
| 3306771 | 8/1984 | Fed. Rep. of Germany | 544/363 |
| 3306772 | 8/1984 | Fed. Rep. of Germany | 544/363 |
| 2085875 | 5/1982 | United Kingdom | 544/363 |

Primary Examiner—Glennon H. Hollrah
Assistant Examiner—James H. Turnipseed
Attorney, Agent, or Firm—Sprung Horn Kramer & Woods

[57] ABSTRACT

The invention relates to 7-amino-1-cyclopropyl-6,8-difluoro-1,4-dihydro-4-oxo-quinoline-3-carboxylic acids, processes for their preparation and compositions containing them as antibacterial agents. Also included in the invention are methods for treating bacterial infection using the compounds and compositions of the invention.

17 Claims, No Drawings

7-AMINO-1-CYCLOPROPYL-6,8-DIFLUORO-1,4-DIHYDRO-4-OXO-QUINOLINE-3-CARBOXYLIC ACIDS AND ANTIBACTERIAL AGENTS CONTAINING THESE COMPOUNDS

The present invention relates to new 7-amino-1-cyclopropyl-6,8-difluoro-1,4-dihydro-4-oxoquinoline-3-carboxylic acids, processes for their preparation and antibacterial agents containing these compounds.

7-Amino-1-cyclopropyl-6,8-difluoro-1,4-dihydro-4-oxoquinoline-3-carboxylic acids of the formula (I)

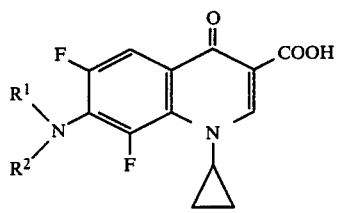

in which
$R^1$ and $R^2$ can be identical or different and represent a $C_1$-$C_4$-alkyl radical which is optionally substituted by a hydroxyl, amino, methylamino or dimethylamino group, and $R^1$ and $R^2$, together with the nitrogen atom to which they are bonded, can furthermore form a 5-membered or 6-membered heterocyclic ring which can additionally contain, as a ring member, the atoms or groups —O—, —S—, —SO—, —SO$_2$— or >N-$R^3$ and which can be optionally monosubstituted, disubstituted or trisubstituted at the carbon atoms by $C_1$-$C_4$- alkyl, hydroxyl, alkoxy having 1-3 carbon atoms, amino, methylamino or ethylamino, and each carbon atom can carry only one substituent, and $R^3$ represents hydrogen, a branched or straightchain alkyl, alkenyl or alkinyl group which has 1 to 6 carbon atoms and can be optionally substituted by a hydroxyl, trifluoromethylmercapto, alkoxy, alkylmercapto, alkylamino or dialkylamino group having 1 to 3 carbon atoms per alkyl radical, the cyano group or the alkoxycarbonyl group having 1 to 4 carbon atoms in the alcohol part, or represents the benzyloxycarbonyl group, a phenylalkyl group which has up to 4 carbon atoms in the aliphatic part and is optionally substituted in the phenyl radical, a phenyl radical which is optionally monosubstituted or disubstituted by hydroxyl, methoxy, chlorine or fluorine, a phenylacyl radical which is optionally monosubstituted or disubstituted by hydroxyl, methoxy, chlorine and fluorine, an oxoalkyl radical having up to 6 carbon atoms and a cycloalkyl-alkyl radical having up to 6 carbon atoms in the cyclic part and up to 3 carbon atoms in the acyclic part, and furthermore denotes a radical $COR^4$, CN or $SO_2R^5$, wherein
$R^4$ represents hydrogen or straight-chain or branched alkyl which has 1 to 4 C atoms and is optionally substituted by 1 or 2 substituents from the series comprising amino, alkoxycarbonyl having 1 to 3 carbon atoms in the alkyl part, carboxyl, alkoxy having 1 to 3 carbon atoms and trifluoromethylthio, or represents phenyl which is optionally substituted by chlorine, hydroxyl, amino or carboxyl, or represents alkoxy having 1 to 4 C atoms, alkylthio having 1 or 2 C atoms, benzyloxy or amino, or represents alkylamino which has 1 to 5 C atoms and is optionally substituted by alkoxycarbonyl having 1 to 3 C atoms in the alkyl part or carboxyl, and $R^5$ represents straight-chain or branched alkyl having 1 to 3 C atoms, phenyl or methylphenyl, and their pharmaceutically useful salts, have been found. They are therefore suitable as active compounds in medicine including the treatment of fish.

Preferred compounds of the formula (I) are those in which
$R^1$ and $R^2$ can be identical or different and represent a $C_1$-$C_3$-alkyl radical which is optionally substituted by a hydroxyl or amino group, and $R^1$ and $R^2$, together with the nitrogen atom to which they are bonded, can furthermore form a 5-membered or 6-membered heterocyclic ring which can additionally contain, as a ring member, the atoms or groups —O—, —S—, —SO$_2$—or >N-$R^3$ and can be optionally monosubstituted or disubstituted at the carbon atoms by $C_1$-$C_3$-alkyl, hydroxyl, amino or methylamino, and each carbon atom can carry only one substituent, and $R^3$ represents hydrogen or a branched or straight-chain alkyl, alkenyl or alkinyl group which has 1 to 4 carbon atoms and can be optionally substituted by a hydroxyl, trifluoromethylmercapto, alkoxy or alkylmercapto group having 1 to 2 carbon atoms per alkyl radical, the cyano group or the alkoxycarbonyl group having 1 to 3 carbon atoms in the alcohol part, or represents the benzyloxycarbonyl group, a phenylalkyl group which has up to 2 carbon atoms in the aliphatic part and is optionally substituted in the phenyl radical by nitro or amino, or represents a phenacyl radical, an oxoalkyl radical having up to 5 carbon atoms and a cycloalkyl-alkyl radical having up to 6 carbon atoms in the cyclic part and up to 2 carbon atoms in the acyclic part, and furthermore denotes a radical $COR^4$, CN or $SO_2R^5$, wherein $R^4$ denotes hydrogen or straight-chain or branched alkyl which has 1 to 3 C atoms and is optionally substituted by 1 or 2 substituents from the series comprising amino, methoxycarbonyl, carboxyl, alkoxy having 1 or 2 carbon atoms or trifluoromethylthio, or denotes phenyl which is optionally substituted by chlorine or hydroxyl, or denotes alkoxy having 1 to 3 C atoms, amino, or alkylamino which has 1 to 5 C atoms and is optionally substituted by alkoxycarbonyl having 1 or 2 C atoms in the alkyl part or carboxyl, and $R^5$ denotes methyl, ethyl, phenyl or methylphenyl.

Particularly preferred compounds of the formula (I) are those
in which
$R^1$ and $R^2$ can be identical or different and represent a $C_1$-$C_2$-alkyl radical which is optionally substituted by a hydroxyl group, and $R^1$ and $R^2$, together with the nitrogen atom to which they are bonded, furthermore can form a 6-membered heterocyclic ring which can additionally contain, as a ring member, the group N-$R^3$ and can be optionally monosubstituted or disubstituted at the carbon atoms by $C_1$-$C_2$-alkyl or hydroxyl, and each carbon atom can carry only one substituent, and $R^3$ represents hydrogen or a branched or straightchain alkyl, alkenyl or alkinyl group which has 1 to 3 carbon atoms and can be optionally substituted by a hydroxyl group or the alkoxycarbonyl group having 1 or 2 carbon atoms in the alcohol part, or represents a benzyl group which is optionally substituted in the phenyl radical by amino, or represents a phenacyl radical, an oxoalkyl radical having up to 4 carbon atoms and a cyclopropylmethyl radical, and furthermore denotes a radical $COR^4$ or $SO_2R^5$, wherein $R^4$ denotes hydrogen, alkyl which has 1 or 2 C atoms and is optionally substituted by a substituent from the series comprising amino and carboxyl, or denotes alkoxy having 1 or 2 C atoms or benzyloxy, and $R^5$ denotes methyl.

Furthermore, it has been found that 7-amino-1-cyclopropyl-6,8-difluoro-1,4-dihydro-4-oxoquinoline-3-carboxylic acids of the formula (I) are obtained when the trifluoro-quinolonecarboxylic acid of the formula (II)

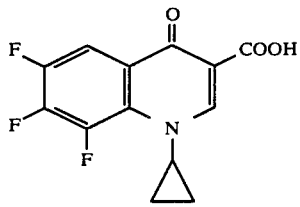

(II)

is reacted with amines of the formula (III)

(III)

in which $R^1$ and $R^2$ have the meaning given above, if appropriate in the presence of acid-binding agents (method A).

Compounds according to the invention, of the formula (I), can also be obtained by a process in which a 7-piperazinylquinolonecarboxylic acid of the formula (IV)

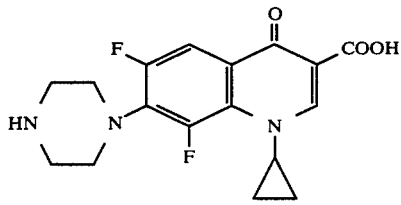

(IV)

in which the piperazinyl radical can be monosubstituted, disubstituted or trisubstituted at the carbon atoms by $C_1$–$C_4$-alkyl, and each carbon atom can carry only one substituent, is reacted with compounds of the formula (V)

$R^3X$  (V)

in which $R^3$ has the meaning given above but cannot be hydrogen, and

X denotes fluorine, chlorine, bromine, iodine, acyloxy, ethoxy, phenoxy or 4-nitrophenoxy, in the presence of acid-binding agents (method B).

Compounds according to the invention, of the formula (I) are also obtained when a 7-piperazinyl-quinolonecarboxylic acid of the formula (IV), in which the piperazinyl radical can be monosubstituted to trisubstituted at the carbon atom by $C_1$-$C_4$-alkyl, and each carbon atom can carry only one substituent, is reacted with anhydrides of the formula (VI)

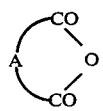

(VI)

in which

A denotes an optionally substituted alkylene chain having 2 or 3 carbon atoms, or an arylene radical, to give the compounds according to the invention, of the formula (Ia) (method C),

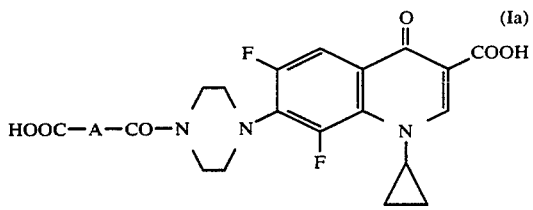

(Ia)

in which the piperazinyl radical can be monosubstituted to trisubstituted at the carbon atoms by $C_1$-$C_4$-alkyl, and each carbon atom can carry only one substituent.

Compounds according to the invention, of the formula (I), can also be obtained when a 7-piperazinyl-quinolonecarboxylic acid of the formula (IV), in which the piperazinyl radical can monosubstituted to trisubstituted at the carbon atoms by $C_1$–$C_4$-alkyl, and each carbon atom can carry only one substituent, is reacted with Michael acceptors of the formula (VII)

$B-CH=CH_2$  (VII)

in which

B represents CN, $CO-R^6$ or $COOR^7$, wherein $R^6$ represents methyl or ethyl and $R^7$ represents methyl, ethyl, n- or i-propyl or benzyl (method D).

If, in the reaction according to method A, 2-methylpiperazine and 1-cyclopropyl-6,7,8-trifluoro-4-oxo-1,4-dihydroquinoline-3-carboxylic acid (II) are used as starting materials, the course of the reaction can be represented by the following equation:

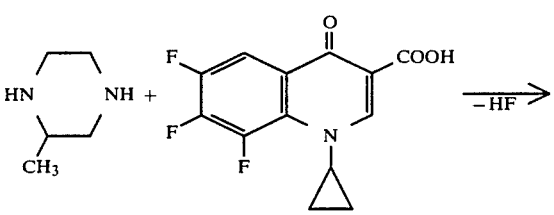

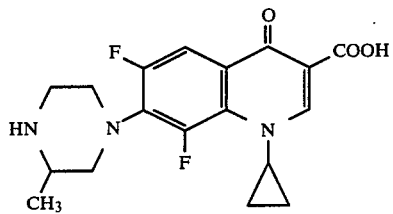

If, in the reaction according to method B, ethyl iodide and 1-cyclopropyl-6,8-difluoro-1,4-dihydro-4-oxo-7-(piperazin-1-yl)-quinoline-3-carboxylic acid are used as starting materials, the course of the reaction can be represented by the following equation:

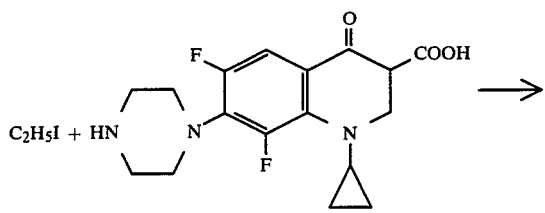

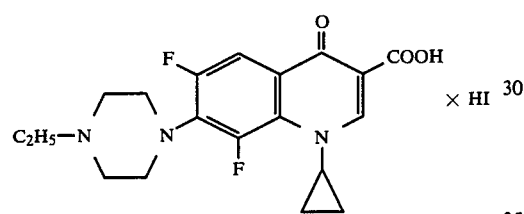

If, for example, in the reaction of (IV) with (V) according to method B, 1-cyclopropyl-6,8-difluoro-1,4-dihydro-4-oxo-7-(piperazin-1-yl)-quinoline-3-carboxylic acid and acetic anhydride are used as starting compounds, the course of the reaction can be represented by the following equation:

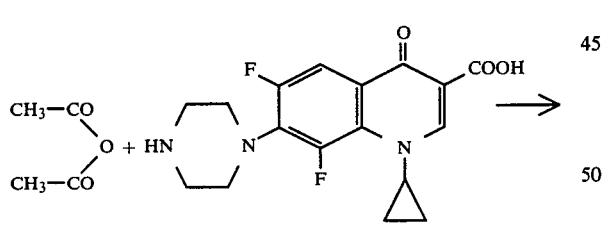

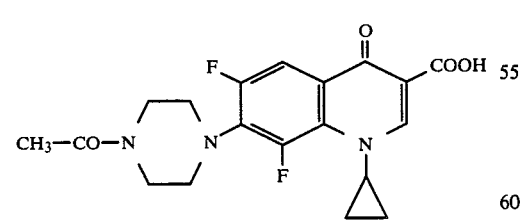

If, for example, the reaction of (I) with (VI) according to method C, 1-cyclopropyl-6,8-difluoro-1,4-dihydro-4-oxo-7-(piperazin-1-yl)-quinoline-3-carboxylic acid and succinic anhydride are used as starting compounds, the course of the reaction can be represented by the following equation:

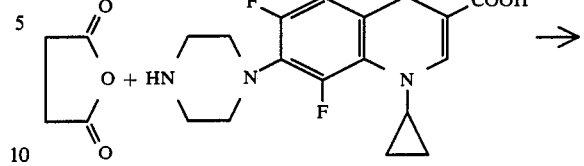

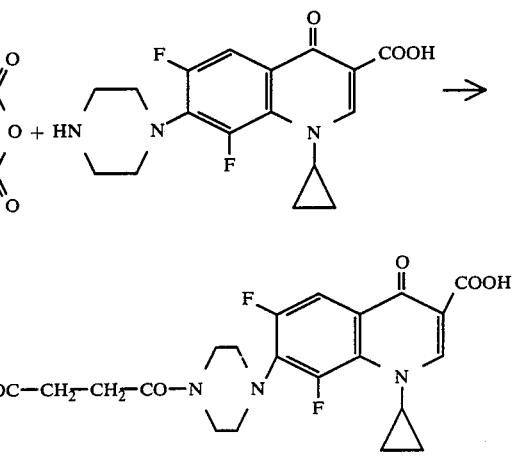

If, for example, in the reaction of (I) with (VII) according to method D, 1-cyclopropyl-6,8-difluoro-1,4-dihydro-4-oxo-7-(piperazin-1-yl)-quinoline-3-carboxylic acid and methyl vinyl ketone are used as starting compounds, the course of the reaction can be represented by the following equation:

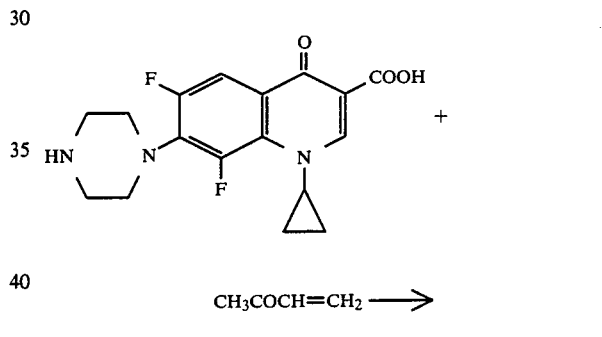

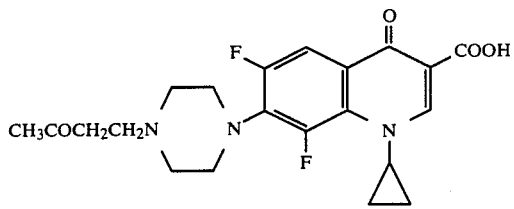

The 1-cyclopropyl-6,7,8-trifluoro-1,4-dihydro-4-oxoquinoline-3-carboxylic acid, of the formula (II), which can be used as starting materials according to method A can be prepared in accordance with the following equation:

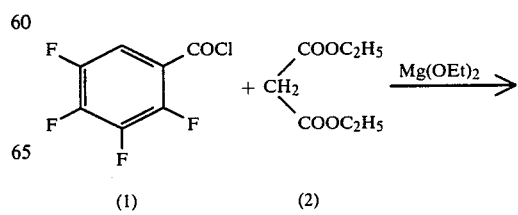

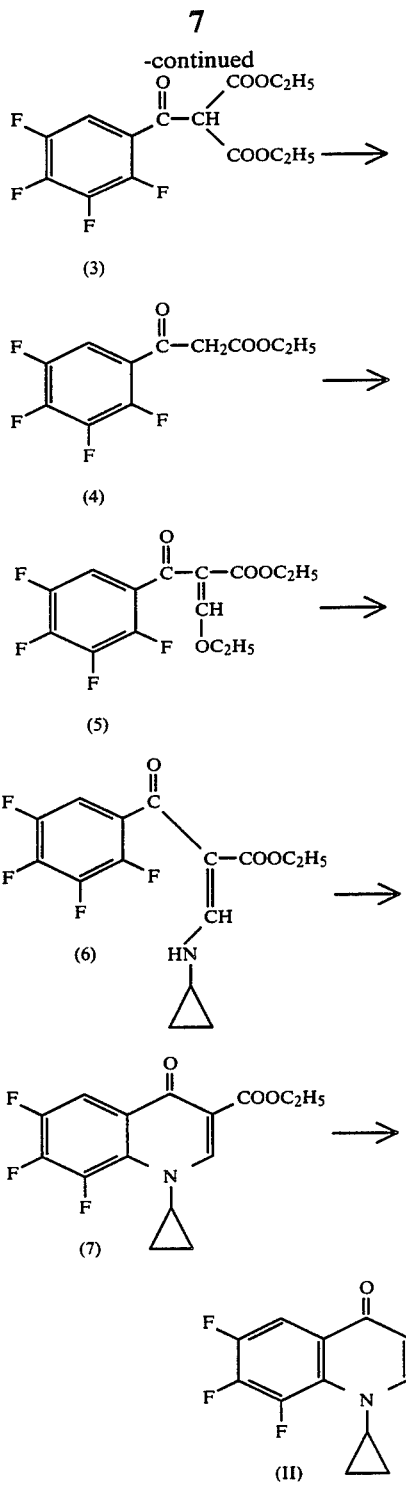

fluorobenzoyl)-3-ethoxy-acrylate (5). The reaction of (5) with cyclopropylamine in a solvent, such as, for example, methylene chloride, alcohol, chloroform, cyclohexane or toluene, leads to the desired intermediate product (6) in a slightly exothermic reaction.

The cyclisation reaction (6)→(7) is carried out in a temperature range from about 60 to 300° C., preferably 80° to 180° C.

Dioxane, dimethyl sulphoxide, N-methylpyrrolidone, sulpholane, hexamethylphosphoric acid triamide and, preferably, N,N-dimethylformamide can be used, for example, as diluents.

Suitable acid-binding agents for this reaction stage include potassium tert.-butylate, butyl-lithium, phenyllithium, phenyl magnesium bromide, sodium methylate, sodium hydride, sodium carbonate, potassium carbonate and, particularly preferably, potassium fluoride and sodium fluoride. It can be advantageous to employ an excess of 10 mol % of base.

The ester hydrolysis of (7) under basic or acidic conditions, which takes place in the last step, leads to 1-cyclopropyl-6,7,8-trifluoro-1,4-dihydro-4-oxoquinoline-3-carboxylic acid (II).

The 2,3,4,5-tetrafluorobenzoyl chloride (1) used as a starting material for this synthesis route was obtained in a customary manner from 2,3,4,5-tetrafluorobenzoic acid, which is known from the literature (G. G. Yakobson, V. N. Odinokov and N. N. Vorozhtsov Jr., Journal of General Chemistry of the USSR in English translation, 36 (1966), 144, using thionyl chloride. It has a boiling point of 75°–80° C./17 mbar. 2,3,4,5-Tetrafluorbenzoyl fluoride has a boiling point of 46° to 47° C. 20 mbar ($n_D^{20}$: 1.4375).

The amines (III) used as starting materials are known, or can be obtained by methods which are known from the literature. The following may be mentioned as examples: morpholine, piperidine, thiomorpholine, pyrrolidine, dimethylamine, ethyl-methylamine, piperazine, N-methylpiperazine, N-ethylpiperazine, N-$\beta$-hydroxyethylpiperazine, N-formylpiperazine, 2-methylpiperazine, 1,2-dimethylpiperazine, cis- and trans-2,5-dimethyl-piperazine, cis- and trans-2,6-dimethylpiperazine, 2-ethylpiperazine, 2-propylpiperazine, 2-isopropylpiperazine and 2-isobutylpiperazine.

The compounds of the formula (V) which are used as starting materials are known. The following may be mentioned as examples:

methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-hexyl bromide.

Formic acetic anhydride, acetic anhydride, propionic anhydride, acetyl chloride, chloroacetyl chloride, dichloroacetyl chloride, bromoacetyl bromide, butyryl chloride, 4-chlorobutyryl chloride, isobutyryl chloride, 3-methylbutanoyl chloride, benzoyl chloride, 3-chlorobenzoyl chloride, 4-fluorobenzoyl chloride, 4-nitrobenzoyl chloride, 4-methylbenzoyl chloride, succinic acid monomethyl ester monochloride, trifluormethylthioacetyl fluoride, 4-nitrophenyl N-(tert.-butoxycarbonyl-glycine, 4-nitro-phenyl N-(tert.-butoxycarbonyl-glycine, 4-nitrophenyl N-(tert.-butoxycarbonyl)-L-alanine, 4-nitrophenyl N-(tert.-butoxycarbonyl)-L-leucine, 4-nitrophenyl N-(tert.butoxycarbonyl)-L-valine, 3-

According to this method diethyl malonate (2) is acylated with 2,3,4,5-tetrafluorobenzoyl chloride (1) in the presence of magnesium methylate to give the aroylmalonate (3), Instead of (1), the 2,3,4,5-tetrafluorobenzoyl fluoride can also be used.

Partial hydrolysis and decarboxylation of (3) in an aqueous medium using catalytic amounts of sulphuric acid or p-toluenesulphonic acid give a good yield of the ethyl aroylacetate (4), which is converted with triethyl o-formate/acetic anhydride to ethyl 2-(2,3,4,5-tetramethoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamoyl chloride, methanesulphonyl chloride, ethanesulphonyl chloride, propane-1-sulphonyl chloride, benzenesulphonyl chloride, 4-toluenesulphonyl chloride, butane-1-sulphonyl chloride and dichlorofluoromethanesulphonyl chloride.

The anhydrides (VI) which can be used according to the invention are known. The following may be mentioned as examples:

succinic anhydride, methylsuccinic anhydride, glutaric anhydride, phthalic anhydride and tetrachlorophthalic anhydride.

The compounds of the formula (VII) which can be used according to the invention are known. The following may be mentioned as examples:

acrylonitrile, methyl vinyl ketone, methyl acrylate, ethyl acrylate and benzyl acrylate.

The reaction of (II) with (III) according to method A is preferably carried out in a diluent, such as dimethyl sulphoxide, N,N-dimethylformamide, hexamethylphosphoric acid triamide, sulpholane, water, an alcohol, such as methanol, ethanol, n-propanol, isopropanol or glycol monomethyl ether, or pyridine. Mixtures of these diluents can also be used.

All customary inorganic and organic acid-binding agents can be used as acid-binding agents. These preferably include the alkali metal hydroxides, alkali metal carbonates, organic amines and amidines. The following may be mentioned individually as being particularly suitable: triethylamine, 1,4-diaza-bicyclo[2.2.2]octane (DABCO), excess amine (III) or 1,8-diazabicyclo[5.4.0]undec-7-ene (DBU).

The reaction temperatures can be varied within a relatively wide range. In general, the reaction is carried out at between about 20° and 200° C., preferably between 80° and 180° C.

The reaction can be carried out under atmospheric pressure but may also be carried out under elevated pressure. In general, it is carried out under pressures between about 1 and about 100 bar, preferably between 1 and 10 bar.

In carrying out the process according to the invention, 1 to 15 mol, preferably 1 to 6 mol, of the amine (III) are employed per mol of the carboxylic acid (II).

The reaction of (IV) with (V) is preferably carried out in a diluent, such as dimethyl sulphoxide, dioxane, N,N-dimethylformamide, hexamethyl-phosphoric acid triamide, sulpholane, water, an alcohol, such as methanol, ethanol, n-propanol, isopropanol or glycol monomethyl ether, or pyridine. Mixtures of these diluents can also be used.

All customary inorganic and organic acid-binding agents can be used as acid-binding agents. These preferably include the alkali metal hydroxides, alkali metal carbonates, organic amines and amidines. The following may be mentioned individually as being particularly suitable: triethylamine, 1,4-diazabicyclo[2.2.2]octane (DABCO) or 1,8-diazabicyclo[5.4.0]undec-7-ene (DBU).

The reaction temperatures can be varied within a relatively wide range. In general, the reaction is carried out at between about 20° and 180° C., preferably between 40 and 110° C.

The reaction can be carried out under atmospheric pressure but may also be carried out under elevated pressure. In general, it is carried out under pressures between about 1 and about 100 bar, preferably between 1 and 10 bar.

In carrying out the process according to the invention by method B, 1 to 4 mol, preferably 1 to 1.5 mol, of the compound (V) are employed per mol of the compound (IV).

The reaction of (IV) with (VI) (method C) is carried out in a diluent, such as N,N-dimethylformamide, dioxane, tetrahydrofuran, pyridine or water, or in mixtures of these diluents. The reaction temperatures can be varied within a relatively wide range. In general, the reaction is carried out at between about 0° C. and about 140° C., preferably between 10° and 100° C.

The reaction can be carried out under atmospheric pressure but may also be carried out under elevated pressure. In general, it is carried out under pressures between about 1 and about 100 bar, preferably between 1 and 10 bar.

All customary inorganic and organic acid-binding agents can be used as the acid-binding agent. These preferably include the alkali metal hydroxides, alkali metal carbonates, pyridine and tert.-amines, such as triethylamine and 1,4-diazabicyclo[2.2.2]octane.

In carrying out the process according to the invention, 1 to 3 mol, preferably 1 to 1.3 mol, of the compound (VI) are employed per mol of the compound (IV).

The reaction (IV) with (VII) (method D) is preferably carried out in a diluent, such as dioxane, dimethyl sulphoxide, N,N-dimethylformamide, methanol, ethanol, isopropanol, n-propanol or glycol monomethyl ether or in mixtures of these solvents.

The reaction temperatures can be varied within a relatively wide range. In general, the reaction is carried out at between about 20° C. and about 150° C., preferably between 50° C. and 100° C.

The reaction can be carried out under atmospheric pressure but may also be carried out under elevated pressure. In general, it is carried out under pressures between about 1 and about 100 bar, preferably between 1 and 10 bar.

In carrying out the process according to the invention, 1 to 5 mol, preferably 1 to 2 mol, of compound (VII) are employed per mol of the compound (IV). A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Also, metal salts of the active compounds of Formula (I) are contemplated, formed by standard methods involving reaction with a metal base. Particularly included are alkali, alkaline earth and ammonium salts of said carboxylic acids of Formula (I).

The following may be mentioned individually as new active compounds:

1-cyclopropyl-6,8-difluoro-1,4-dihydro-4-oxo-7-(piperazin-1-yl)-quinoline-3-carboxylic acid, 1-cyclo propyl-6,8-difluoro-1,4-dihydro-4-oxo-7-(4-methylpiperazin-1-yl)-quinoline-3-carboxylic acid, 1-cyclopropyl-6,8-difluoro-1,4-dihydro- 4-oxo-7-(4-ethylpiperazin-1-yl)-quinoline-3-carboxylic acid, 1-cylcopropyl-6,8-difluoro-1,4-dihydro-4-oxo-7-(3-methylpiperazin-1-yl)-quinoline-3-carboxylic acid, 1-cyclopropyl-6,8-difluoro-1,4-dihydro-4-oxo-7-(3,4-dimethylpiperazin-1-yl)-quinoline-3-carboxylic acid, 1-cyclopropyl-6,8-difluoro-1,4-dihydro-4-oxo-7-(4-ethyl-3-methylpiperazin-1-yl)-quinoline-3-carboxylic acid, 1-cyclopropyl-6,8-difluoro-1,4-dihydro-4-oxo-7-[4-(2-hydroxyethyl)-3-methylpiperazin-1-yl]-quinoline-3-carboxylic acid, 1-cyclo propyl-6,8-difluoro-1,4-dihydro-4-oxo-7-[4-(3-hydroxypropyl)-3-methylpiperazin-1-yl]-quinoline-3-carboxylic acid, 1-cyclopropyl-6,8-difluoro-1,4-dihydro-4-oxo-7-(2,5-dimethylpiperazin-1-yl)-quinoline-3-carboxylic acid, 1-cyclopropyl-6,8-difluoro-1,4-dihydro-4-oxo-7-(4-ethyl-2,5-dimethylpiperazin-1-yl)-quinoline-3-carboxylic acid, 1-cyclopropyl-6,8-difluoro-1,4-dihydro-4-oxo-7-(3,5-dimethylpiperazin-1-yl)-quinoline-3-carboxylic acid, 1-cyclopropyl-6,8-difluoro-1,4-dihydro-4-oxo-7-(3,4,5-trimethylpiperazin-1-yl)-quinoline-3-carboxylic acid, 1-cyclopropyl-6,8-difluoro-1,4-dihydro-4-oxo-7-(4-ethyl-3,5-dimethylpiperazin-1-yl)-quinoline-3-carboxylic acid, 1-cyclopropyl-6,8-difluoro-1,4-dihydro-4-oxo-7-(3-ethylpiperazin-1-yl)-quinoline-3-carboxylic acid, 1-cyclopropyl-6,8-difluoro-1,4-dihydro-4-oxo-7-(3-n-propylpiperazin-1-yl)-quinoline-3-carboxylic acid, 1-cyclopropyl-6,8-difluoro-1,4-dihydro-4-oxo-7-(3-isopropylpiperazin-1-yl)-quinoline-3-carboxylic acid, 1-cyclo propyl-6,8-difluoro-1,4-dihydro-4-oxo-7-(3-isobutylpiperazin-1-yl)-quinoline-3-carboxylic acid, 1-cyclopropyl-6,8-difluoro-1,4-dihydro-4-oxo-(3-methyl-4-n-propylpiperazin-1-yl)-quinoline-3-carboxylic acid, 1-cyclopropyl-6,8-difluoro-1,4-dihydro-4-oxo-7-(3-methyl-4-isopropylpiperazin-1-yl)-quinoline-3-carboxylic acid, 1-cyclopropyl-6,8-difluoro-1,4-dihydro-4-oxo-7-(4-n-butyl-3-methylpiperazin-1-yl)-quinoline-3-carboxylic acid, 1-cyclopropyl-6,8-difluoro-1,4-dihydro-4-oxo-7-morpholinylquinoline-3-carboxylic acid, and their pharmaceutically useful acid addition salts, alkali metal salts, alkaline earth metal salts or hydrates.

PREPARATION EXAMPLES

Example A (Preparation of the starting material II):

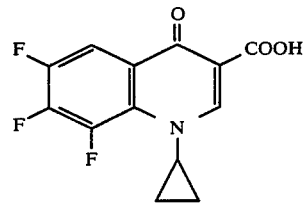

24.g of magnesium turnings are suspended in 50 ml of anhydrous ethanol. 5 ml of carbon tetrachloride are added, and, when the reaction has started, a mixture of 160 g of diethyl malonate, 100 ml of absolute ethanol and 400 ml of anhydrous toluene is added dropwise at 50°-60° C. Thereafter, the mixture is heated to 50°-60° C. for a further hour, and cooled to −5° C. to −10° C. with dry ice acetone, and a solution of 212.5 g of 2,3,4,5-tetrafluorobenzoyl chloride (1) in 80 ml of absolute toluene is slowly added dropwise at this temperature. The mixture is stirred for 1 hour at 0° to −5° C., and is allowed to reach room temperature overnight, and a mixture of 400 ml of ice water and 25 ml of concentrated sulphuric acid is allowed to run in whilst cooling with ice. The phases are separated, and extraction with toluene is repeated twice. The combined toluene solutions are washed with saturated NaCl solution and dried with $Na_2SO_4$, and the solvent is stripped off in vacuo. 335 g of diethyl 2,3,4,5-tetra-fluorobenzoylmalonate (3) are obtained as a crude product.

0.3 g of p-toluenesulphonic acid is added to an emulsion of 284.8 g of crude diethyl 2,3,4,5-tetrafluorobenzoyl-malonate (3) in 300 ml of water. The mixture is heated to the boil for 5 hours, while stirring thoroughly, the cold emulsion is extracted several times with methylene chloride, the combined $CH_2CL_2$ solutions are washed once with saturated NaCl solution and dried with $Na_2SO_4$, and the solvent is distilled off in vacuo. Fractionation of the residue in a fine vacuum gives 160.2 g of ethyl 2,3,4,5-tetrafluorobenzoyl-acetate (4) of boiling point 100°–110° C./0.09–0.1 mbar. Melting point 47°–49° C.

A mixture of 110.7 g of ethyl 2,3,4,5-tetrafluorobenzoylacetate (4), 93.5 g of ethyl o-formate and 107 g of acetic anhydride is heated to 150° C. for 2 hours. Thereafter, the volatile constituents are distilled off under a vacuum from a waterpump and finally under a fine vacuum at a band temperature of ∼120° C. 123.9 g of crude ethyl 2-(2,3,4,5-tetrafluorobenzoyl)-3-ethoxyacrylate (5) remain. It is sufficiently pure for the further reactions.

23.2 g of cyclopropylamine are added dropwise to a solution of 123.9 g of ethyl 2-(2,3,4,5-tetrafluorobenzoyl)-3-ethoxyacrylate (5) in 250 ml of ethanol, while cooling with ice and stirring. When the exothermic reaction has abated, stirring is continued for a further hour at room temperature, the solvent is stripped off in vacuo and the residue is recrystallised from cyclohexane petroleum ether. 115 g of ethyl 2-(2,3,4,5-tetrafluorobenzoyl)-3-cyclopropylamino-acrylate (6) of melting point 63°–65° C. are obtained.

21.2 g of sodium fluoride are added to a solution of 107.8 g of ethyl 2-(2,3,4,5-tetrafluorobenzoyl)-3-cyclopropylamino-acrylate (6) in 400 ml of anhydrous dimethylformamide. Thereafter, the mixture is stirred under reflux for 2 hours, and the hot reaction mixture is poured onto ice. The precipitate is filtered off under suction, washed thoroughly with water and dried over calcium chloride in vacuo at 100° C. 91.2 g of ethyl 1-cyclopropyl-6,7,8-trifluoro-1,4-dihydro-4-oxoquinoline-3-carboxylate (7) of melting point 167°–168° C. are obtained.

A mixture of 94 g of ethyl 1-cyclopropyl-6,7,8-trifluoro-1,4-dihydro-4-oxoquinoline-3-carboxylate (7), 600 ml of glacial acetic acid, 450 ml of water and 70 ml of concentrated sulphuric acid is heated under reflux for 1.5 hours. Thereafter, the hot suspension is poured onto ice, and the precipitate is filtered off under suction, rinsed thoroughly with water and dried in vacuo at 100° C. In this manner, 88.9 g of pure 1-cyclopropyl-6,7,8-trifluoro-1,4-dihydro-4-oxoquinoline-3-carboxylic acid II of melting point 228°–230° C. (decomposition) are obtained.

EXAMPLE 1

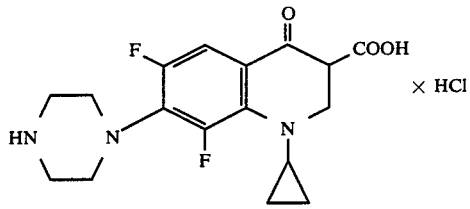

A mixture of 2.83 g (0.01 mol) of 1-cyclopropyl-6,7,8-trifluoro-1,4-dihydro-4-oxoquinoline-3-carboxylic acid (II), 4.4 g (0.051 mol) of anhydrous piperazine and 30 ml of dry pyridine is refluxed for 6 hours. The solvent is stripped off in vacuo, the residue is taken up in 25 ml of water, the pH is adjusted to 1 with concentrated hydrochloric acid, while cooling with ice and, when the mixture is cold, the precipitate is filtered off under suction and washed with cold 10% strength hydrochloric acid and ethanol. After drying in vacuo at 100° C., 3.05 g of 1-cyclopropyl-6,8-difluoro-7-(piperazin-1-yl)-1,4-dihydro-4-oxoquinoline-3-carboxylic acid hydrochloride having a decomposition temperature of 354°–355° C. are obtained.

EXAMPLE 2

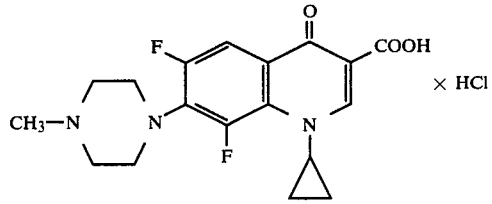

2.83 g (0.01 mol) of II are reacted with 4 g (0.04 mol) of N-methylpiperazine analogously to Example 1, and 3.6 g of 1-cyclopropyl-6,8-difluoro-7-(4-methylpiperazin-1-yl)-1,4-dihydro-4-oxoquinoline-3-carboxylic acid hydrochloride having a decomposition temperature 300°–303° C. are isolated.

The following compounds are obtained analogously to Example 1 or 2:

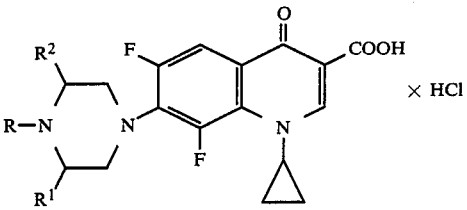

| Example | R | $R^1$ | $R^2$ | Decomposition temperature (°C.) |
|---|---|---|---|---|
| 3 | H | $CH_3$ | H | 325–330 |
| 4 | H | $C_2H_5$ | H | 330–335 |
| 5 | H | $CH_3$ | $CH_3$ | 310–315 |
| 6 | $HO(CH_2)_2-$ | H | H | 290–293 |

EXAMPLE 7

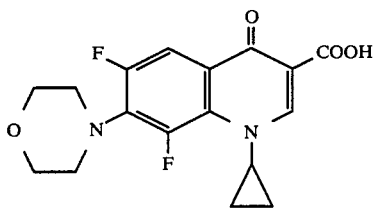

A mixture of 2.83 g (0.01 mol) of 1-cyclopropyl-6,7,8-trifluoro-1,4-dihydro-4-oxoquinoline-3-carboxylic acid, 0.9 g (0.01 mol) of morpholine and 2.3 g of diazabicyclo [2.2.2]octane (0.02 mol) in 35 ml of dimethyl sulphoxide is heated to 140° C. for 5 hours. The solvent is distilled off in vacuo, 50 ml of water are added to the residue, the mixture is acidified with semiconcentrated hydrochloric acid, and, when the mixture is cold, the product is filtered off under suction, washed with water, dried in vacuo and recrystallised from glycol monomethyl ether. 2.4 g of 1-cyclopropyl-6,8-difluoro-7-(morpholin-4-yl)-1,4-dihydro-4-oxoquinoline-3-carboxylic acid having a decomposition temperature of 257°–260° C. are obtained.

The following compounds are obtained analogously to Example 7:

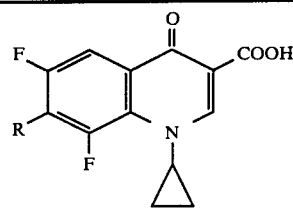

| Example | R | Decomposition temperature (°C.) |
|---|---|---|
| 8 | 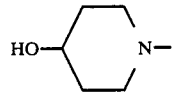 | 227–280 |
| 9 | 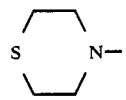 | 291–294 |

-continued

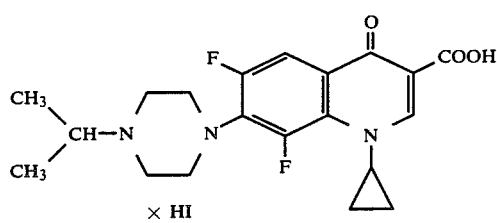

| Example | R | Decomposition temperature (°C.) |
|---|---|---|
| 10 | CH₃-CH(O)-CH(CH₃)-N— (morpholine with methyls) | 241–245 |
| 11 | pyrrolidin-1-yl (N—) | 280–285 |

EXAMPLE 12

A mixture of 3.5 g (0.01 mol) of 1-cyclopropyl-6,8-difluoro- 7-(piperazin-1-yl)-1,4-dihydro-4-oxoquinoline-3-carboxylic acid, 3.4 g (0.02 mol) of isopropyl iodide and 2.1 (0.02 mol) of triethylamine in 50 ml of dimethylformamide is heated to 80° C. in the course of 6 hours. After the solvent has been evaporated off, the residue is stirred with 30 ml of water and is then filtered off under suction, washed with water and recrystallised from methanol. 2.3 g of 1-cyclopropyl-6,8-difluoro-7-(4-isopropylpiperazin-1-yl)-1,4-dihydro-4-oxoquinoline-3-carboxylic acid hydriodide having a decomposition temperature of 306°–308° C. are obtained.

The following compounds are obtained analogously to Example 12:

| Example | R | R¹ | Decomposition temperature (°C.) |
|---|---|---|---|
| 13 | C₂H₅ | H | 289–291° |
| 14 | C₂H₅ | CH₃ | 252–258 |

EXAMPLE 15

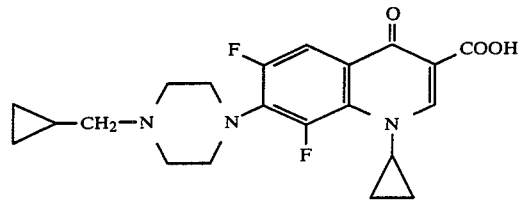

A mixture of 3.5 g (0.01 mol) of 1-cyclopropyl-6,8-difluoro-7-(piperazin-1-yl)-1,4-dihydro-4-oxoquinolinecarboxylic acid, 2.1 g of triethylamine, 1.8 g of cyclopropylmethyl chloride and 3.3 g of potassium iodide is heated to 80° C. for 6 hours. Thereafter, the mixture is evaporated down in vacuo, 30 ml of water are added, the mixture is adjusted to pH 5 and the precipitate is filtered off under suction, washed with water and methanol and recrystallized from glycol monomethyl ether. 1.8 g of 1-cyclopropyl-7-(4-cyclopropylmethylpiperazin-1-yl)-6,8-difluoro-1,4-dihydro-4-oxoquinoline-3-carboxylic acid having a decomposition temperature of 246°–248° C. are obtained.

The following compounds are obtained analogously to Example 15:

| Example | R | Decomposition temperature (°C.) |
|---|---|---|
| 16 | O₂N—⟨C₆H₄⟩—CH₂ | 210–212 |
| 17 | CH₃—CO—CH₂ | 201–204 |
| 18 | ⟨C₆H₅⟩—CO—CH₂ | 210–212 |
| 19 | CH₂=CH—CH₂ | 172–175 |
| 20 | HC≡C—CH₂ | 228–232 (Hydrochloride) |

EXAMPLE 21

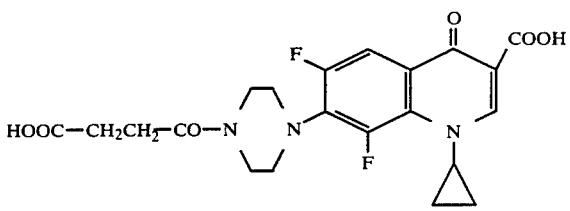

3.5 g (0.01 mol) of 1-cyclopropyl-6,8-difluoro-7-(piperazin-1-yl)-1,4-dihydro-4-oxoquinoline-3-carboxylic acid are dissolved in a mixture of 0.4 g of sodium hydroxide in 20 ml of water, and a solution of 1 g of succinic anhydride in 10 ml of dioxane, and a solution of 0.4 g of sodium hydroxide in 10 ml of water, are simultaneously added dropwise at 20° C. After standing for 12 hours, the mixture is adjusted to pH 5 with 2N hydrochloric acid, and the precipitate is filtered off under suction, washed with water, heated with methanol, filtered off under suction and dried. 2.5 g of 7-[4-(3-carboxypropionyl)-piperazin-1-yl]-1-cyclopropyl-6,8-difluoro-1,4-dihydro-4-oxoquinoline-3-carboxylic acid having a decomposition temperature of 217°-219° C. are obtained.

The following compounds are obtained analogously to Example 21:

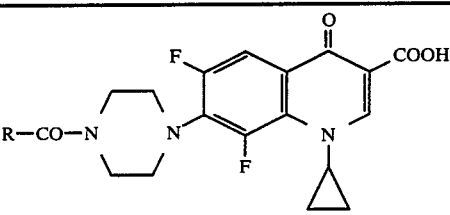

| Example | R | Acylating agent | Decomposition temperature |
|---|---|---|---|
| 22 | H | HCO—O—COCH$_3$ | 295–300 |
| 23 | CH$_3$ | CH$_3$—CO—Cl | 248–251 |
| 24 | n-C$_3$H$_7$ | C$_3$H$_7$—CO—Cl | 182–186 |
| 25 | C$_2$H$_5$O | C$_2$H$_5$O—CO—Cl | 204–208 |
| 26 | CH$_3$—SO$_2$ | CH$_3$—SO$_2$—Cl | 295–296 |

EXAMPLE 27

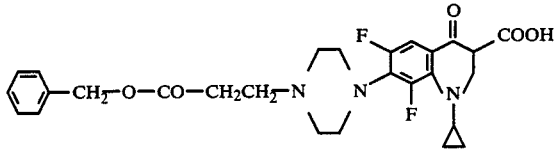

3.5 g (0.01 mol) of 1-cyclopropyl-6,8-difluoro-7-(piperazin-1-yl)-1,4-dihydro-4-oxoquinoline-3-carboxylic acid are heated under reflux with 4 g of benzyl acrylate for 5 hours. The hot solution is filtered, and the precipitate which separates out is filtered off under suction, washed with ethanol and dried. 2.3 g of 7-[4-(2-benzyloxycarbonyl-ethyl)-piperazin-1-yl]-1-cyclopropyl-6,8-difluoro-1,4-dihydro-4-oxoquinoline-3-carboxylic acid having a decomposition temperature of 132°–135° C. are obtained.

EXAMPLE 28

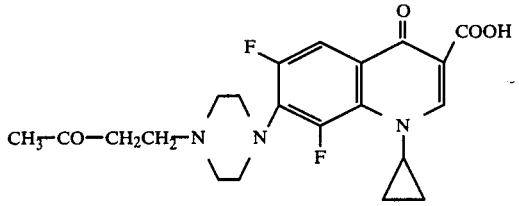

The procedure is carried out analogously to Example 27, using methyl vinyl ketone, and 1-cyclopropyl-6,8-difluoro-1,4-dihydro-4-oxo-7-[4-(3-oxobutyl)-piperazin-1-yl]-quinoline-3-carboxylic acid having a decomposition temperature of 155°–158° C. are obtained.

The compounds according to the invention couple low toxicity with a broad antibacterial spectrum against Gram-positive and Gram-negative bacteria, in particular against Enterobacteriaceae; especially against those which are resistant to various antibiotics, such as, for example, penicillins, cephalosporins, aminoglycosides, sulphonamides and tetracyclins.

These valuable properties permit their use as chemotherapeutic active compounds in medicine and as compounds for preserving inorganic and organic materials, in particular organic materials of all kinds, for example polymers, lubricants, paints, fibres, leather, paper and timber, foodstuffs and water.

The active compounds according to the invention are active against a very broad spectrum of micro-organisms. They can be used to combat Gram-negative and Gram-positive bacteria and bacteria-like micro-organisms and to treat illnesses caused by tnese pathogens.

The active compounds according to the invention are particularly active against bacteria and bacteria-like micro-organisms. They are therefore particularly suitable for the treatment of local and systemic infections, caused by these pathogens, in medicine.

For example, local and/or systemic illnesses caused by the following pathogens or by mixtures of the following pathogens can be treated and/or prevented:

Micrococcaceae, such as Staphylococci, for example *Staphylococcus aureus* and Staph. epidermidis (Staph.=-Staphylococcus); Lactobacteriaceae, such as Streptococci, for example Streptococcus pyogenes, α-, or β-haemolytic Streptococci, non-(γ)-haemolytic Streptococci, Enterococci and *Diplococcus pneumoniae* (Pneumococci) (Str.=Streptococcus); Enterobacteriaceae, such as Escherichiae bacteria of the Coli group: Escherichia bacteria, for example *Escherichia coli*, Enterobacter bacteria, for example aerogenes and *E. cloacae*, Klebsiella bacteria, for example K. pneumoniae, Serratia, for example Serratia marcescens (E.=Enterobacter) (K.=Klebsiella), Proteae bacteria of the Proteus group: Proteus, for example Proteus vulgaris, Pr. morganii, Pr. rettgeri and Pr. mirabilis (Pr.=Proteus);

Pseudomonadaceae, such as Pseudomonas bacteria, for example *Pseudomonas aeruginosa* (PS.=Pseudomonas);

Bacteroidaceae, such as Bacteroides bacteria, for example Bacteroides fragilis (B.=Bacteroides); Mycoplasma, for example, *Mycoplasma pneumoniae*.

The above list of pathogens is purely illustrative and is in no way to be intepreted as restrictive.

The following may be mentioned as examples of illnesses which can be treated by the active compounds according to the invention:

Illnesses of the respiratory passages and of the pharyngeal cavity; otitis; pharyngitis; pneumonia; peritonitis; pyelonephritis; cycstitis; endocarditis; systemic infections; bronchitis; arthritis; local infections and septic diseases.

The present invention includes pharmaceutical preparations which in addition to non-toxic, inert pharmaceutically suitable excipients contain one or more compounds according to the invention or which consists of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance correspond to a fraction or a multiple of an individual dose.

The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) resorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium meta-hydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably about 0.5 to 95, % by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example by mixing the active compound or the active compounds with the excipient or excipients.

The active compounds or the pharmaceutical preparations can be administered locally, orally, parenterally, intraperitoneally and/or rectally, preferably orally or parenterally, as well as intravenously or intramuscularly.

In general it has proved advantageous in medicine to administer the active compound or compounds according to the invention in total amounts of about 0.5 to about 500, preferably 5 to 100, mg/kg of body weight every 24 hours, optionally in the form of several individual administrations, in order to achieve the desired results. An individual administration contains the active compound or compounds according to the invention preferably in amounts of about 1 to about 250, especially 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

The new compounds can be administered in the customary concentrations and formulations, together with the feedstuff or the feedstuff preparations, or in the drinking water. Consequently, an infection caused by Gram-negative or Gram-positive bacteria can be treated with the result that promotion of growth and an improvement in the utilisation of the feedstuff can be achieved.

The MIC values of some of the compounds according to the invention are given in the table below.

TABLE

| | MIC mg/ml | | | | | | |
|---|---|---|---|---|---|---|---|
| Strain | Example 13 | Example 3 | Example 5 | Example 4 | Example 12 | Example 8 | Example 28 |
| E. Coli Neumann | 0,015 | 0,015 | 0,015 | 0,015 | 0,06 | 0,015 | 0,015 |
| E. Coli 455/7 | 4 | 8 | 8 | 8 | 16 | 8 | 8 |
| Klebsiella 63 | 0,03 | 0,015 | 0,015 | 0,06 | 0,125 | 0,125 | 0,015 |
| Klebsiella 8085 | 0,015 | 0,015 | 0,015 | 0,015 | 0,03 | 0,015 | 0,015 |
| Proteus mir. 8223 | 4 | 4 | 4 | 8 | 16 | 4 | 4 |
| Proteus vulg. 1017 | 0,06 | 0,03 | 0,06 | 0,06 | 0,5 | 0,06 | 0,015 |
| Proteus morg. 932 | 0,015 | 0,015 | 0,015 | 0,015 | 0,06 | 0,03 | 0,015 |
| Staph. aur. 133 | 0,25 | 0,125 | 0,125 | 0,125 | 0,25 | 0,015 | 0,25 |
| Streptococc. faecal. 9790 | 1 | 0,5 | 0,5 | 0,5 | 2 | 0,125 | 0,5 |
| Pseudomonas W. | 0,5 | 0,5 | 1 | 1 | 8 | 1 | 0,25 |

| | MIC mg/ml | | | | | | | |
|---|---|---|---|---|---|---|---|---|
| Strain | Example 1 | Example 2 | Example 11 | Example 15 | Example 14 | Example 6 | Example 7 | Example 10 |
| E. coli Neumann | 0,015 | 0,015 | 0,06 | 0,03 | 0,015 | 0,015 | 0,015 | 0,125 |
| E. coli 455/7 | 4 | 1 | 128 | 16 | 16 | 8 | 16 | 32 |
| Klebsiella 63 | 0,015 | 0,015 | 0,5 | 0,125 | 0,03 | 0,03 | 0,06 | 0,5 |
| Klebsiella 8085 | 0,015 | 0,015 | 0,125 | 0,03 | 0,015 | 0,015 | 0,03 | 0,25 |
| Proteus mir. 8223 | 2 | 2 | 8 | 8 | 16 | 4 | 8 | 8 |
| Proteus vulg. 1017 | 0,015 | 0,03 | 1 | 0,5 | 0,25 | 0,06 | 0,25 | 1 |
| Proteus morg. 932 | 0,015 | 0,015 | 0,5 | 0,06 | 0,03 | 0,015 | 0,06 | 1 |
| Staph. aur. 133 | 0,125 | 0,125 | 0,03 | 0,25 | 0,125 | 0,06 | 0,03 | 0,015 |
| Streptococc. faecal. 9790 | 0,25 | 0,5 | 0,5 | 2 | 1 | 0,5 | 0,5 | 0,25 |
| Pseudomonas W. | 0,06 | 0,125 | 4 | 8 | 4 | 1 | 1 | 4 |

Agar dilution test
Isosensitest medium
Denley multipoint inoculator

We claim:
1. A 7-amino-1-cyclopropyl-6,8-difluoro-1,4-dihydro-4-oxo-quinolinecarboxylic acid of the formula (I)

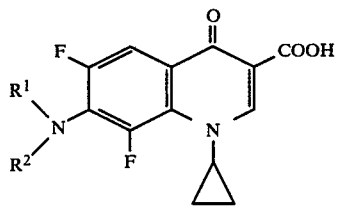

in which
$R^1$ and $R^2$ are identical or different and represent a $C_1$-$C_4$-alkyl radical which is optionally substituted by a hydroxyl, amino, methylamino or dimethylamino group, and $R^1$ and $R^2$, together with the nitrogen atom to which they are bonded, furthermore form a 5-membered or 6-membered heterocyclic ring, which can additionally have, as a ring member, the atoms or groups —O—, —S—, —SO—, —SO$_2$— or >N-$R^3$ and which is optionally monosubstituted, disubstituted or trisubstituted at the carbon atoms by $C_1$-$C_4$-alkyl, hydroxyl, alkoxy having 1-3 carbon atoms, amino, methylamino or ethylamino, and each carbon atom carries no more than one substituent, and $R^3$ represents hydrogen, a branched or straight-chain alkyl, alkenyl or alkinyl group which has 1 to 6 carbon atoms and is optionally substituted by a hydroxyl, trifluoromethylmercapto, alkoxy, alkylmercapto, alkylamino or dialkylamino group having 1 to 3 carbon atoms per alkyl radical, the cyano group or the alkoxycarbonyl group having 1 to 4 carbon atoms in the alcohol part, or represents the benzyloxycarbonyl group, a phenylalkyl group which has up to 4 carbon atoms in the aliphatic part and is optionally substituted in the phenyl radical by nitro or amino, a phenyl radical which is optionally monosubstituted or disubstituted by hydroxyl, methoxy, chlorine or fluorine, a phenylacyl radical which is optionally monosubstituted or disubstituted by hydroxyl, methoxy, chlorine and fluorine, an oxoalkyl radical having up to 6 carbon atoms and a cycloalkyl-alkyl radical having up to 6 carbon atoms in the cyclic part and up to 3 carbon atoms in the acyclic part, and furthermore denotes a radical COR$^4$, CN or SO$_2$R$^5$,
wherein
$R^4$ represents hydrogen or straight-chain or branched alkyl which has 1 to 4 C atoms and is optionally substituted by 1 or 2 substituents selected from amino, alkoxycarbonyl having 1 to 3 carbon atoms in the alkyl part, carboxyl, alkoxy having 1 to 3 carbon atoms and trifluoromethylthio, or represents phenyl which is optionally substituted by chlorine, hydroxyl, amino or carboxyl, or represents alkoxy having 1 to 4 C atoms, alkylthio having 1 or 2 C atoms, benzyloxy or amino, or represents alkylamino which has 1 to 5 C atoms and is optionally substituted by alkoxycarbonyl having 1 to 3 C atoms in the alkyl part or carboxyl, and
$R^5$ represents straight-chain or branched alkyl having 1 to 3 C atoms, phenyl or methylphenyl, and its pharmaceutically useful salts.
2. A 7-amino-1-cyclopropyl-6,8-difluoro-1,4-dihydro-4-oxo-quinolinecarboxylic acid of claim 1 of the formula (I)

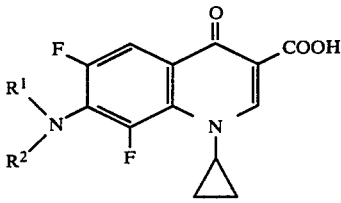

in which
R[1] and R[2] are identical or different and represent a C$_1$-C$_3$-alkyl radical which is optionally substituted by a hydroxyl or amino group, and R[1] and R[2], together with the nitrogen atom to which they are bonded, form a 5-membered or 6-membered heterocyclic ring which can additionally contain, as a ring member, the atoms or groups —O—, —S—, —SO$_2$— or >N-R[3] and can be optionally monosubstituted or disubstituted at the carbon atoms by C$_1$-C$_3$-alkyl, hydroxyl, amino or methylamino, and each carbon atom can carry only one substituent, and R[3] represents hydrogen or a branched or straight-chain alkyl, alkenyl or alkinyl group which has 1 to 4 carbon atoms and can be optionally substituted by a hydroxyl, trifluoromethylmercapto, alkoxy or alkylmercapto group having 1 to 2 carbon atoms per alkyl radical, the cyano group or the alkoxycarbonyl group having 1 to 3 carbon atoms in the alcohol part, or represents the benzyloxycarbonyl group, a phenylalkyl group which has up to 2 carbon atoms in the aliphatic part and is optionally substitued in the phenyl radical by nitro or amino, or represents a phenacyl radical, an oxoalkyl radical having up to 5 carbon atoms and a cycloalkylalkyl radical having up to 6 carbon atoms in the cyclic part and up to 2 carbon atoms in the acyclic part, and furthermore denotes a radical COR[4], CN or SO$_2$R[5], wherein R[4] denotes hydrogen or straight-chain or branched alkyl which has 1 to 3 C atoms and is optionally substituted by 1 or 2 substituents selected from the group consisting of amino, methoxycarbonyl, carboxyl, alkoxy having 1 or 2 carbon atoms or trifluoromethylthio, or denotes phenyl which is optionally substituted by chlorine or hydroxyl, or denotes alkoxy or alkylamino which has 1 to 5 C atoms and is optionally substituted by alkoxycarbonyl having 1 or 2 C atoms in the alkyl part or carboxyl, and R[5] denotes methyl, ethyl, phenyl or methylphenyl.

3. A 7-amino-1-cyclopropyl-6,8-difluoro-1,4-dihydro-4-oxo-quinolinecarboxylic acid of claim 1 of the formula (I)

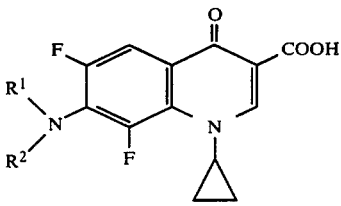

in which
R[1] and R[2] can be identical or different and represent a C$_1$-C$_2$-alkyl radical which is optionally substituted by a hydroxyl group, and R[1] and R[2], together with the nitrogen atom to which they are bonded, furthermore can form a 6-membered heterocyclic ring which can additionally contain, as a ring member, the group N-R[3] and can be optionally monosubstituted or disubstituted at the carbon atoms by C$_1$-C$_2$-alkyl or hydroxyl, and each carbon atom can carry only one substituent, and R[3] represents hydrogen or a branched or straight-chain alkyl, alkenyl or alkinyl group which has 1 to 3 carbon atoms and can be optionally substituted by a hydroxyl group or the alkoxycarbonyl group having 1 or 2 carbon atoms in the alcohol part, or represents a benzyl group which is optionally substituted in the phenyl radical by amino, or represents a phenacyl radical, an oxoalkyl radical having up to 4 carbon atoms and a cyclopropylmethyl radical, and furthermore denotes a radical COR[4] or SO$_2$R[5], wherein R[4] denotes hydrogen, alkyl which has 1 or 2 C atoms and is optionally substituted by a substituent selected from amino and carboxyl, or denotes alkoxy having 1 or 2 C atoms or benzyloxy, and R[5] denotes methyl.

4. A compound of claim 1 which is 1-cyclopropyl-6,8-difluoro-7-(piperazin-1-yl)-1,4-dihydro-4-oxoquinoline-3-carboxylic acid.

5. A compound of claim 1 which is 1-cyclopropyl-6,8-difluoro-7-(4-methylpiperazin-1-yl)-1,4-dihydro-4-oxoquinoline-3-carboxylic acid.

6. A compound of claim 1 which is 1-cyclopropyl-6,8-difluoro-7-(3-methylpiperazin-1-yl)-1,4-dihydro-4-oxoquinoline-carboxylic acid.

7. A compound of claim 1 which is 1-cyclopropyl-6,8-difluoro-7-(4-ethylpiperazin-1-yl)-1,4-dihydro-4-oxoquinoline-3-carboxylic acid.

8. A compound of claim 1 which is 1-cyclopropyl-6,8-difluoro-7-[4-(3-oxobutyl)-piperazin-1-yl]-1,4-dihydro-4-oxoquinoline-3-carboxylic acid.

9. A compound of claim 1 which is 1-cyclopropyl-6,8-difluoro-7-(pyrrolidin-1-yl)-1,4-dihydro-4-oxoquinoline-3-carboxylic acid.

10. A pharmaceutical composition containing as an active ingredient an antibacterially effective amount of a compound of claim 1 in admixture with an inert pharmaceutical carrier.

11. A pharmaceutical composition containing as an active ingredient an antibacterially effective amount of a compound of claim 1 in the form of a sterile or physiologically effective isotonic aqueous solution.

12. A composition of claim 10 containing from 0.5 to 90% by weight of the said active ingredient.

13. A pharmaceutical in dosage unit form comprising an antibacterially effective amount of a compound of claim 1 and an inert pharmaceutical carrier.

14. A medicament of claim 13 in the form of tablets, pills, dragees, capsules, ampoules or suppositories.

15. A method of combatting bacterial infection in warm-blooded animals which comprises administering to said animals an antibacterially effective amount of an active compound of claim 1 either alone, in admixture with a diluent or in the form of a medicament.

16. A method of claim 1 in which the active compound is administered in an amount of about 0.05 to about 100 mg/kg of body weight per day.

17. A method of claim 16 in which the active compound is administered in an amount of about 0.1 to about 10 mg/kg of body weight per day.

* * * * *

UNITED STATES PATENT AND TRADEMARK OFFICE
CERTIFICATE OF CORRECTION

PATENT NO. : 4,556,658  
DATED : December 3, 1985  
INVENTOR(S) : Klaus Grohe, et al.

Page 1 of 2

It is certified that error appears in the above-identified patent and that said Letters Patent is hereby corrected as shown below:

| | |
|---|---|
| Title Page, No. 54, 3rd line and Col. 1, line 3 | After "ACIDS" insert --,-- |
| Col. 7, line 61 | After "(3)" delete "," and substitute --.-- |
| Col. 11, lines 17, 31, 53 | After "cyclo" insert -- - -- |
| Col. 12, line 14 | After "24." insert --3-- |
| Col. 12, line 40 | Delete "$CH_2CL_2$" and substitute --$CH_2Cl_2$-- |
| Col. 14, line 59, Example 8 | First line under second column delete "227-280" and substitute --277-280-- |
| Col. 16, line 15 and Col. 24, line 32 | Before "carboxylic" insert -- 3- -- |
| Col. 17, line 5 | After "-car" insert -- - -- |
| Col. 18, line 16 | Delete "tnese" and substitute --these-- |
| Col. 19, line 2 | Delete "7/8" and substitute -- 1/3 -- |

UNITED STATES PATENT AND TRADEMARK OFFICE
CERTIFICATE OF CORRECTION

PATENT NO. : 4,556,658

DATED : December 3, 1985

INVENTOR(S) : Klaus Grohe, et al

It is certified that error appears in the above-identified patent and that said Letters Patent is hereby corrected as shown below:

Col. 23, line 33          Correct spelling of "substituted"

Col. 24, line 52          After "pharmaceutical" insert --composition--

Signed and Sealed this

Fourth Day of November, 1986

[SEAL]

Attest:

DONALD J. QUIGG

Attesting Officer          Commissioner of Patents and Trademarks

UNITED STATES PATENT AND TRADEMARK OFFICE
CERTIFICATE OF CORRECTION

PATENT NO. : 4,556,658
DATED : December 3, 1985
INVENTOR(S) : Klaus Grohe et al.

It is certified that error appears in the above-identified patent and that said Letters Patent is hereby corrected as shown below:

| | |
|---|---|
| Col. 5, line 20, Col. 13, line 25 and Col. 17, line 35 | Add bonding line in right side of formula as follows: |
| Col. 17, line 5 | Delete "car" and substitute --carb-- |
| Col. 17, line 6 | Delete "boxypropionyl" and substitute --oxypropionyl-- |
| Col. 22, line 3 | Delete "mon-" and substitute --mono-- |
| Col. 22, line 4 | Delete "osubstituted" and substitute --substituted-- |
| Col. 23, line 16 | Delete "heter-" and substitute --hetero-- |
| Col. 23, line 17 | Delete "ocyclic" and substitute --cyclic-- |
| Col. 23, line 21 | Delete "C3" and substitute --$C_3$-- |

Signed and Sealed this

Twenty-seventh Day of January, 1987

Attest:

DONALD J. QUIGG

Attesting Officer     Commissioner of Patents and Trademarks ated REEXAMINATION CERTIFICATE (759th)

United States Patent [19]

Grohe et al.

[11] B1 4,556,658

[45] Certificate Issued    Sep. 15, 1987

[54] 7-AMINO-1-CYCLOPROPYL-6,8-DIFLUORO-1,4-DIHYDRO-4-OXO-QUINOLINE-3-CARBOXYLIC ACIDS AND ANTIBACTERIAL AGENTS CONTAINING THESE COMPOUNDS

[75] Inventors: Klaus Grohe, Odenthal; Uwe Petersen, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

Reexamination Request:
No. 90/000,981, Apr. 7, 1986

Reexamination Certificate for:
Patent No.: 4,556,658
Issued: Dec. 3, 1985
Appl. No.: 603,480
Filed: Apr. 24, 1984

Certificate of Correction issued Jan. 27, 1987.

[30] Foreign Application Priority Data

May 18, 1983 [DE]   Fed. Rep. of Germany ....... 3318145

[51] Int. Cl.$^4$ .......................................... A61K 31/495
[52] U.S. Cl. .................................... 514/254; 514/222; 514/236; 514/256; 514/312; 544/58.6; 544/63; 544/96; 544/128; 544/358; 544/363; 546/156; C07D/401/04

[58] Field of Search ............. 544/363, 128, 358, 58.6, 544/63, 96; 546/156; 514/254, 222, 236, 256, 312

[56] References Cited

U.S. PATENT DOCUMENTS

| | | | |
|---|---|---|---|
| 3,149,104 | 9/1964 | Lesher et al. | 546/156 |
| 4,398,029 | 8/1983 | Irikura et al. | 544/363 |
| 4,429,127 | 1/1984 | Irikura et al. | 544/363 |
| 4,448,962 | 5/1984 | Irikura et al. | 544/363 |

FOREIGN PATENT DOCUMENTS

| | | | |
|---|---|---|---|
| 2939786 | 4/1980 | Fed. Rep. of Germany | 544/363 |
| 3106013 | 9/1982 | Fed. Rep. of Germany | . |
| 3306771 | 8/1984 | Fed. Rep. of Germany | 544/363 |
| 3306772 | 8/1984 | Fed. Rep. of Germany | 544/363 |
| 3441788A-1 | 6/1986 | Fed. Rep. of Germany | . |
| 0049355 | 4/1982 | European Pat. Off. | . |
| 0078362 | 5/1983 | European Pat. Off. | . |
| 2085875 | 5/1982 | United Kingdom | 544/363 |

OTHER PUBLICATIONS

Felmingham et al., "Drugs Exptl. Clin. Res.", vol. XI(5), 1985, pp. 317-329.
Shrire et al., "Eur. J. Clin. Microbiol.", vol. 3(4), 1984, pp. 328-332.
Wise et al., "Antimicrobial Agents and Chemotherapy", vol. 23, Apr. 1983, pp. 559-564.

*Primary Examiner*—James H. Turnipseed

[57] ABSTRACT

The invention relates to 7-amino-1-cyclopropyl-6,8-difluoro-1,4-dihydro-4-oxo-quinoline-3-carboxylic acids, processes for their preparation and compositions containing them as antibacterial agents. Also included in the invention are methods for treating bacterial infection using the compounds and compositions of the invention.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-17 is confirmed.

* * * * *